United States Patent [19]

Maeyama

[11] Patent Number: 4,929,825
[45] Date of Patent: May 29, 1990

[54] MEANS FOR DETECTING DAMAGE TO THE CARD CONNECTING THE PHOTOSENSOR AND MAIN BODY PULSIMETER

[75] Inventor: Hachiro Maeyama, Nara, Japan
[73] Assignee: Tsuyama Mfg. Co., Ltd., Osaka, Japan
[21] Appl. No.: 230,294
[22] Filed: Aug. 8, 1988
[30] Foreign Application Priority Data

Aug. 7, 1987 [JP] Japan .................. 62-121946[U]

[51] Int. Cl.$^5$ .............................................. G01V 9/04
[52] U.S. Cl. ..................................... 250/221; 128/666
[58] Field of Search ............... 128/664, 666, 687, 689, 128/690, 665; 364/413.03; 250/221, 574

[56] References Cited

U.S. PATENT DOCUMENTS

| | | | |
|---|---|---|---|
| 3,815,583 | 6/1974 | Scheit | 128/666 |
| 4,186,390 | 1/1980 | Enemark | 250/574 |
| 4,305,401 | 12/1981 | Reissmueller et al. | 128/690 |
| 4,425,921 | 1/1984 | Fujisaki et al. | 128/664 |

Primary Examiner—David C. Nelms
Attorney, Agent, or Firm—Allegretti & Witcoff, Ltd.

[57] ABSTRACT

A pulsimeter comprises a pulse sensor portion including a light emitting diode and a photodiade, and a main body, the pulse sensor portion and the main body being connected through a cord. The main body includes a received light comparing circuit for comparing a quantity of light received by the photodiode with a predetermined valve, and a display device for displaying a result of the comparison. If there is no abnormality in the cord and the pulse sensor portion in normal condition is not in contact with a human body, the quantity of received light in increased to cause a light emitting diode of the display device to be turned on. On the other hand, if there is any abnormality in the cord or the pulse sensor portion, the quantity of received light is not increased and the light emitting diode is not turned on. While the pulsimeter in normal condition is being used, the light emitting diode is not turned on because of light transmission through the human body. However, if short circuit occurs in the cord, the received light comparing circuit is operated as if it is operated by an increase in the quantity of received light, causing the light emitting diode to be turned on.

7 Claims, 4 Drawing Sheets

MEANS FOR DETECTING DAMAGE TO THE CARD CONNECTING THE PHOTOSENSOR AND MAIN BODY PULSIMETER

BACKGROUND OF THE INVENTION

1. Field of the Invention

The present invention relates to a pulsimeter and particular to a pulsimeter having a photosensor for measuring, by a photoelectric conversion system, the pulse of a person to be examined.

2. Description of the Prior Art

Pulsimeters in the prior art have various methods for measuring pulse. Particularly, pulsimeters of a photoelectric conversion system have been proposed as this system enables measurement without externally hurting the examined human body.

Such a pulsimeter of the photoelectric conversion system measures the pulse by utilizing light transmittance through the human body, which changes according to change in bloodstream in capillaries because the bloodstream in the blood vessel periodically changes according to pulsation of the heart.

FIG. 1 is a block diagram showing an overall construction of such a conventional pulsimeter of the photoelectric conversion system.

Referring to FIG. 1, an electric signal generated in a light emitting portion drive circuit 1 contained in the main body of the pulsimeter is transmitted to a pulse sensor portion 2 including a photosensor through a cord, to cause a light emitting portion 3 of a light emitting diode to emit light. The photosensor 2 has the light emitting diode 3 and a photodiode 4 as a light receiving portion facing each other. The photosensor 2 is used in a manner in which an earlobe or finger of a person to be examined is held therebetween. The reason for using the photosensor 2 for such an end part of a human body is that little error occurs in measurement of such an end part which is hardly affected by movements of the muscle and the thickness of which is hardly changed. The light transmitted through the earlobe or the like is received by the photodiode 4, where it is converted to an electric signal according to the quantity of received light. The electric signal is applied to a filter circuit 7 contained in the main body of the pulsimeter through a cord. The electric signal, from which a DC component caused by unnecessary light such as external light is removed in the filter circuit 7, is then AC-amplified in an AC amplifier 9 and thus pulse-shaped. A changing cycle of the AC-amplified signal output is measured by a pulse cycle measuring device 10 and then a pulse rate is evaluated by a CPU 11, whereby the evaluated value is indicated on a display device 12.

In such a conventional pulsimeter as described above, the pulse sensor portion including the photosensor, and the main body including a detection circuit, an evaluation circuit and the like are usually connected through a cord for convenience of use. Consequently, the cord is bent or pulled dependent on the state of use or the frequency of use and as a result breaking of the core wire, short circuit or the like might occur.

However, if a trouble of the core wire occurs, it sometimes happens that a pulse rate is represented as having been measured on a display device although it is indicated by unusual numerals. Accordingly, it is sometimes difficult for the operator to judge whether the pulse rate represented by unusual numerals is caused by any trouble in the core wire or any disorder in the examined person. Therefore, it is likely to occur that such an erroneous pulse rate is treated as data of the examined person.

SUMMARY OF THE INVENTION

An object of the present invention is to provide a pulsimeter having high reliability.

Another object of the present invention is to provide a pulsimeter capable of checking a core wire of a cord connected thereto for occurrence of trouble.

Still another object of the present invention is to provide a pulsimeter capable of automatically detecting breaking of a core wire of a cord connected thereto.

In order to accomplish the above described objects, a pulsimeter according to the present invention comprises a pulse sensor portion, a main body and indication means. The pulse sensor portion includes a photosensor formed by a light emitting portion and a light receiving portion and the photosensor is used in direct contact with a human body. The main body measures pulse based on a quantity of light received by the light receiving portion. The indication means is operated when the quantity of light exceeds a predetermined value, to give an indication.

In the pulsimeter thus constructed, the quantity of light received by the light receiving portion exceeds the predetermined value in a state in which the photosensor is not in contact with a human body, if there is no trouble in the cord connecting the photosensor and the main body. Thus, it can be determined dependent on operation of the indication means whether a trouble in the cord occurs or not.

These objects and other objects, features, aspects and advantages of the present invention will become more apparent from the following detailed description of the present invention when taken in conjunction with the accompanying drawings.

DESCRIPTION OF THE PREFERRED EMBODIMENT

Figure 1:
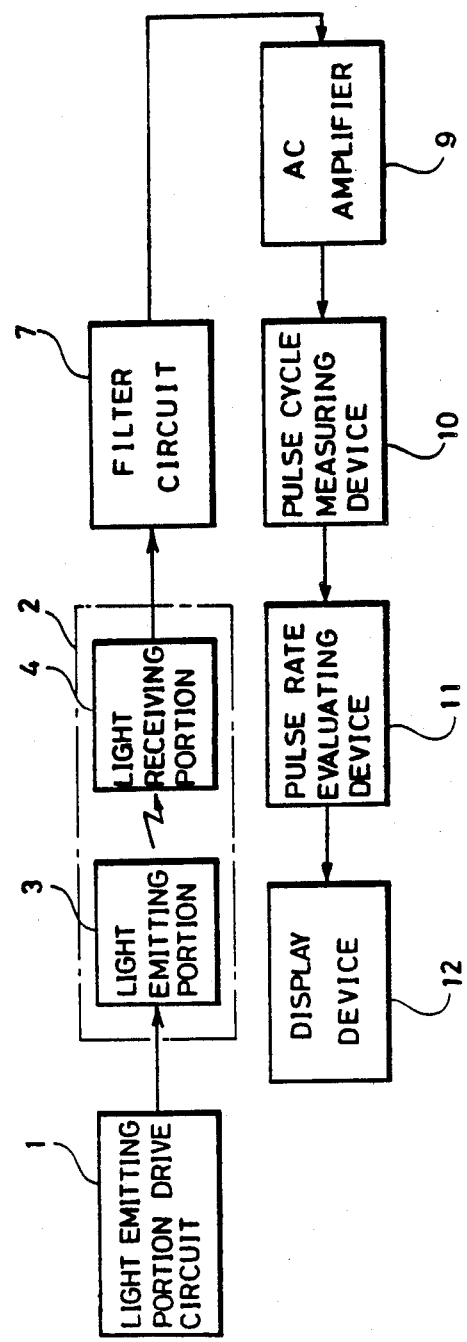
FIG. 1 is a block diagram of an overall construction of a conventional pulsimeter of a photoelectric conversion system.
Figure 2:
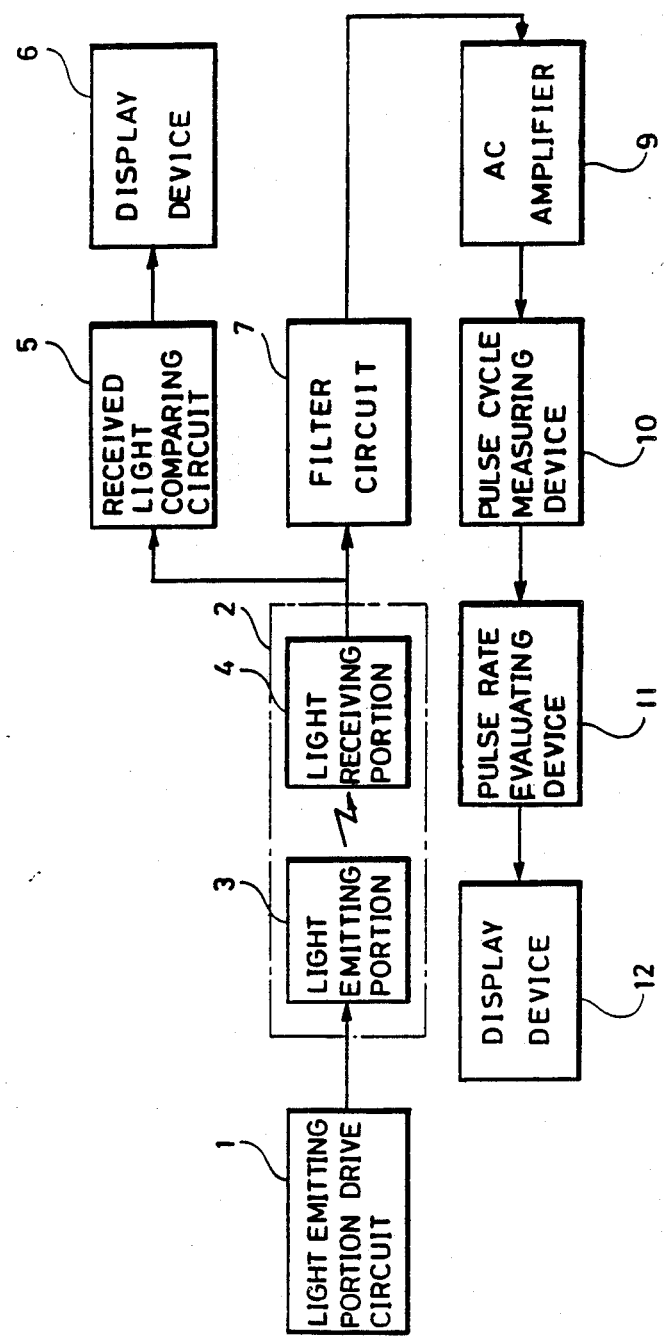
FIG. 2 is a block diagram showing an overall construction of an embodiment of the present invention.
Figure 3:
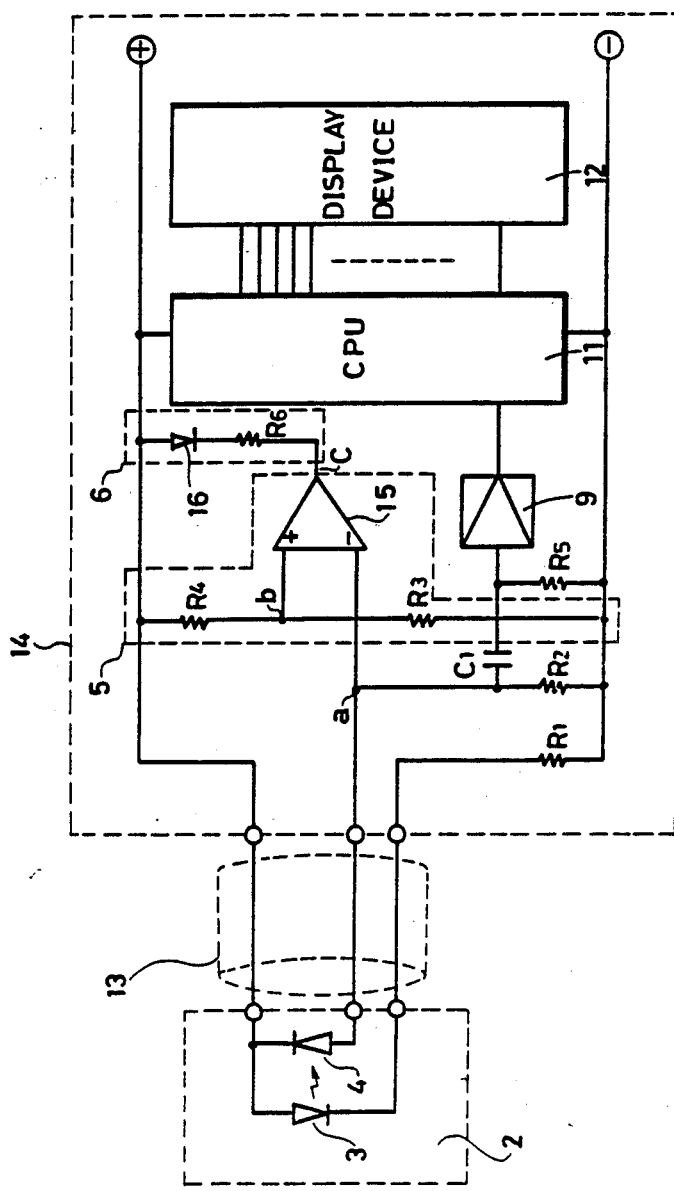
FIG. 3 is a circuit diagram showing a concrete construction of a main part of the block diagram in FIG. 2.
Figure 4:
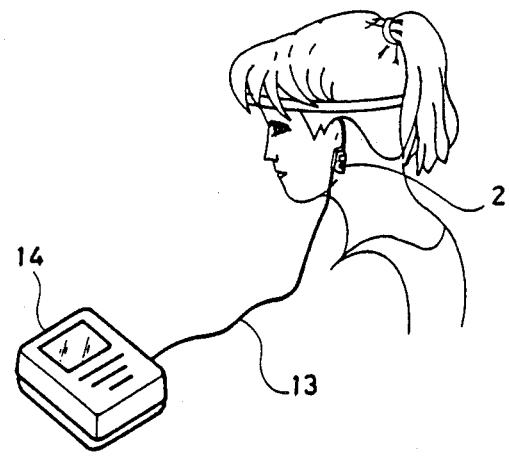
FIG. 4 is a schematic perspective view showing a typical example of use of a pulsimeter according to the present invention.
Figure 5:
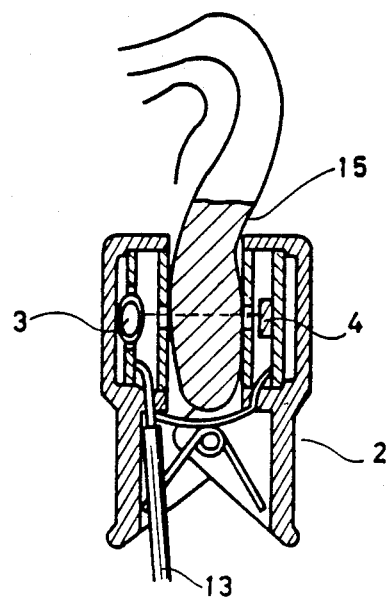
FIG. 5 is an enlarged sectional view around the pulse sensor portion of the pulsimeter shown in FIG. 4.

Referring to FIGS. 2 to 5, a pulsimeter comprises a pulse sensor portion 2 and a main body 14 which are connected through a cord 13 as shown in FIG. 4. An electric signal generated in a light emitting portion drive circuit 1 contained in the main body 14 of the pulsimeter is transmitted to the pulse sensor portion 2 comprising a photosensor through the cord 13, to turn on a light emitting diode 3. The photosensor has a clip-shaped form including the light emitting diode 3 and a photodiode 4 opposed to each other, and it is used in a manner in which an earlobe or finger or the like of a person to be examined is held therebetween as shown in FIG. 4. The reason for using the photosensor for an end part of the human body is that such part is hardly affected by movements of the muscle and the thickness thereof is not varied, causing little error in measurement. The light transmitted through the earlobe or the like is received by the photodiode 4, where it is converted to an electric signal according to the quantity of received light. The electric signal is received by a filter circuit 7 (comprising a capacitor C1 and a resistor R5) contained in the main body 14 of the pulsimeter through the cord 13 in the same manner as in a conventional pulsimeter. According to the present invention, there are further provided a received light comparing circuit 5 for comparing the quantity of received light with a predetermined value based on the electric signal and a display device 6 for displaying the result of comparison. The received light comparing circuit 5 comprises resistors R3 and R4, and a comparator for comparing a potential at a point b determined by the resistors R3 and R4 and a potential at a point a indicating an output of received light. The display device 6 comprises a light emitting diode 16 and a resistor R6 connecting an output point c of the comparator and a potential $\oplus$.

On the other hand, a DC component caused by unnecessary light such as external incident light is removed from the electric signal in the filter circuit 7 and then electric signal is AC-amplified in an AC amplifier 9 and thus pulse-shaped. A changing cycle of an output of the signal thus amplified and pulse-shaped is measured by a pulse cycle measuring device 10 and the pulse rate is evaluated in a CPU 11, whereby the evaluated value is displayed as the pulse rate on the display device 12, in the same manner as in a conventional pulsimeter.

Now, description is made of operation of the received light comparing circuit 5 and the display device 6 of the pulsimeter thus constructed.

First, let us assume a case in which a power supply of the main body 14 of the pulsimeter is turned on and the pulse sensor 2 is not yet in contact with a human body. In this case, if there is no abnormality in the cord 13, that is, if normal conduction is held without any breaking in a core wire of the cord, a quantity of light received in the light receiving portion 4 is highly increased because transmittance between the light emitting portion 3 and the light receiving portion 4 is not lowered if the pulse sensor 2 is in normal condition. As a result, the potential at the point a is excessively increased. Since the potential at the point b is set in advance and is not changed, the point c on the output side of the comparator 15 falls to a low level when the potential at the point a exceeds the potential at the point b. Thus, the light emitting diode 16 is turned on and non-existence of abnormality in the cord 13 can be determined by confirmation of the turn-on of the light emitting diode 16.

If the pulse sensor portion 2 is not in normal condition although no abnormality exists in the cord 13, that is, in cases where the light emitting portion 3 does not emit light normally or the light receiving portion 4 cannot receive light normally if no abnormality exists in the light emitting portion 3, the potential at the point a does not increase because a value of current flowing through the point a is not increased. As a result, the point c on the output side of the comparator 15 rises to a high level and the light emitting diode 16 is not turned on. Thus, before the pulsimeter is used, determination as to whether a trouble occurs in the cord 13 as well as the pulse sensor portion 2 connected thereto can be made dependent on turn-on of the light emitting diode 16.

While the pulsimeter is being used, the light emitting diode 16 is not turned on because the potential at the point b is set to a value higher than the potential at the point a determined by a quantity of light transmitted through the earlobe or the like of the human body if the pulsimeter is in normal condition. Accordingly, if the light emitting diode 16 is turned on during the use of the pulsimeter, it means that the electric current at the point a is increased due to short circuit of the core wire in the cord 13. Thus, occurrence of short circuit in the cord 13 during the use of the pulsimeter can also be detected based on turn-on of the light emitting diode 16.

Although the light emitting diode 16 is turned on or turned off in the above described embodiment as a result of comparing the potential at the point a based on the current amount in the light receiving portion with the predetermined potential, the comparison may be made between electric current generated in the light receiving portion and a predetermined current, not based on the potentials.

Although the light emitting diode 16 is used as the display device 6 in the above described embodiment, the display method is not limited thereto. For example, an output of the comparator 15 is supplied to the CPU 11 and an increase or decrease of the quantity of received light may be indicated directly on a display device 12. In addition, a buzzer may be sounded instead of or together with the display. In other words, insofar as an increase or decrease of the quantity of received light can be indicated reliably, there is no limitation in the method and the place of indication thereof.

As described above in connection with the embodiment, the present invention is adapted to enable the indication means to indicate that a quantity of light received by the light receiving portion of the photosensor exceeds a predetermined value when such exceeding occurs. Consequently, the pulsimeter according to the present invention makes it easy to determine whether or not a trouble occurs in the cord connected to the main body thereof and to the photosensor and thus it has high reliability.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulsimeter comprising:
   a pulse sensor portion including a photosensor formed by a light emitting portion and a light receiving portion, said photosensor adapted for contact with a human body,
   a main body for measuring pulse of the human body based on a quantity of light received by said light receiving portion,
   means connecting the photosensor and the main body, and
   indication means for indicating when said quantity of light exceeds a predetermined value, to give an indication of damage to the means connecting the photosensor and the main body.

2. A pulsimeter in accordance with claim 1, wherein said quantity of light is converted to an electric signal in said light receiving portion.

3. A pulsimeter in accordance with claim 2, wherein said indication means comprises comparing means for comparing a level of said electric signal with a predetermined reference level, and display means responsive to an output of said comparing means for indicating that the level of said electric signal is higher than said predetermined reference level.

4. A pulsimeter in accordance with claim 3, wherein said comparing means includes a comparator.

5. A pulsimeter in accordance with claim 3, wherein said display means includes a light emitting diode.

6. A pulsimeter in accordance with claim 1, wherein, said means connecting said photosensor and said main body includes a cord connected at one end to said pulse sensor portion and at the other end to said main body.

7. A pulsimeter for measuring the pulse of a human comprising:

a pulse sensor portion including a photosensor formed by a light emitting portion and a light receiving portion, said photosensor being adapted for contact with a human body.

a main body for measuring a pulse of the human body based on a quantity of light received by said light receiving portion, means connecting the pulse sensor portion and the means body, received light comparing means for comparing the quantity of received light with a predetermined value, and display means for displaying the result of the comparison, whereby when the photosensor is not mounted on the human body and the quantity of light received by the light receiving portion exceeds said predetermined value, the user can determine the condition of the means connecting the pulse sensor portion and the main body.

* * * * *